US00PP16761P3

(12) United States Plant Patent
Lintott

(10) Patent No.: US PP16,761 P3
(45) Date of Patent: Jul. 4, 2006

(54) ***CHRYSANTHEMUM* PLANT NAMED 'HEADLINER PINK'**

(50) Latin Name: *Chrysanthemum morifolium*
Varietal Denomination: Headliner Pink

(75) Inventor: Keith G. Lintott, Bognor Regis (GB)

(73) Assignee: Cleangro, Ltd, Chichester (GB)

( * ) Notice: Subject to any disclaimer, the term of this patent is extended or adjusted under 35 U.S.C. 154(b) by 41 days.

(21) Appl. No.: 11/055,277

(22) Filed: Feb. 9, 2005

(65) Prior Publication Data

US 2005/0177915 P1 Aug. 11, 2005

Related U.S. Application Data

(60) Provisional application No. 60/543,816, filed on Feb. 11, 2004.

(51) Int. Cl.
*A01H 5/00* (2006.01)

(52) U.S. Cl. ..... Plt./297

(58) Field of Classification Search ..... Plt./297, Plt./292

See application file for complete search history.

(56) References Cited

PUBLICATIONS

Royal Van Zanten Gardenmum Catalog 2002 listing the variety 'Dove'. See, e.g., pp. 5 (photograph) and 9.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Headliner Pink,' having a domed capitulum of small round pink single type flowers and a round habit. Flowers last well under adverse weather conditions.

1 Drawing Sheet

Latin name of the genus and species: Botanical classification: *Chrysanthemum morifolium.*

Variety denomination: The new *Chrysanthemum* variety denomination is 'Headliner Pink.'

BACKGROUND OF THE INVENTION

The present invention comprises a new and distinct cultivar of *Chrysanthemum* botanically known as *Chrysanthemum morifolium,* and referred to by the variety name 'Headliner Pink.'

'Headliner Pink,' identified as 31184-0, originated from a cross made in a controlled breeding program in Chichester, West Sussex, United Kingdom.

The female parent of the new *Chrysanthemum* variety is an undistributed, unpatented seedling identified as '30697-0.' The male parent of the new *Chrysanthemum* variety is an undistributed, unpatented seedling identified as '30738-0.' The new *Chrysanthemum* variety 'Headliner Pink' has been asexually reproduced by vegetative cuttings in Chichester, West Sussex, United Kingdom and the distinguishing characteristics are retained through successive generations of asexual reproduction.

BRIEF SUMMARY OF THE INVENTION

'Headliner Pink' is a garden type of *Chrysanthemum* plant variety having a domed-round canopy of small round pink single type flowers.

Comparison with Female Parent

Plants of the new *Chrysanthemum* variety 'Headliner Pink' are dissimilar to the parent variety '30697-0' in plant habit and growth rate. However, in side-by-side comparisons in Chichester, West Sussex, United Kingdom, under commercial practice, plants of the new *Chrysanthemum* variety 'Headliner Pink' differed from plants of the parent variety '30697-0' in the following characteristics.

1. The new *Chrysanthemum* variety 'Headliner Pink' produces small pink single type flowers whereas the parent variety '30697-0' produces medium sized pink single type flowers.
2. Plants of the new *Chrysanthemum* variety 'Headliner Pink' have smaller and shorter inflorescence than plants of the parent variety '30697-0.'
3. Plants of the new *Chrysanthemum* variety 'Headliner Pink' are less vigorous than plants of the parent variety '30697-0.'

Comparison with Male Parent

Plants of the new *Chrysanthemum* variety 'Headliner Pink' are dissimilar to the parent variety '30738-0' in plant habit and growth rate. In side-by-side comparisons in Chichester, West Sussex, United Kingdom, under commercial practice, plants of the new *Chrysanthemum* variety 'Headliner Pink' differed from plants of the parent variety '30738-0' in the following characteristics.

1. The new *Chrysanthemum* variety 'Headliner Pink' produces small, pink single type flowers whereas the parent variety '30738-0' produces small, yellow single type flowers.
2. Plants of the new *Chrysanthemum* variety 'Headliner Pink' are more vigorous than plants of the parent variety '30738-0.'
3. Plants of the new *Chrysanthemum* variety 'Headliner Pink' flower near 63 days natural season whereas plants of the parent variety '30738-0' flower near 70 days natural season.

Comparison with the Variety 'Dove'

Plants of the new *Chrysanthemum* variety 'Headliner Pink' are dissimilar to the unpatented variety 'Dove' in plant habit and growth rate. However, in side-by-side comparisons in Chichester, West Sussex, United Kingdom, under commercial practice, plants of the new *Chrysanthemum* variety 'Headliner Pink' differed from plants of the parent variety 'Dove' in the following characteristics.

1. The new *Chrysanthemum* variety 'Headliner Pink' produces small pink single type flowers whereas the variety 'Dove' produces smaller deeper pink single type flowers.
2. Plants of the new *Chrysanthemum* variety 'Headliner Pink' have smaller and shorter inflorescence than plants of the variety 'Dove.'
3. Plants of the new *Chrysanthemum* variety 'Headliner Pink' are less vigorous than plant of the variety 'Dove.'

BRIEF DESCRIPTION OF ILLUSTRATION

Typical specimens of the plant and flowers for the new *Chrysanthemum* variety 'Headliner Pink' are shown in the accompanying digital photograph. The colors shown are as true as possible within the usual limits of this kind of illustration.

FIG. 1 is a whole plant view of the new *Chrysanthemum* variety 'Headliner Pink' grown in a pot. The plant shown in the illustration is 63 days from the commencement of planting outdoors in mid-June.

DETAILED BOTANICAL DESCRIPTION

The following description of the new *Chrysanthemum* variety 'Headliner Pink' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 60° F. to 75° F. during the day under natural light conditions. The plants were grown outdoors in mid-June in 4 liter pots using loamless compost. No growth retardants were used. To produce a commercial product the plants may be pinched once with the center bud removed. The typical container size for commercial growth is 4 liters (8"). It has been observed that the shelf life of the new variety is about 26 days with a response time of about 9 weeks natural season. The new variety is suitable for growth in a temperature range of 50° F. to 75° F.

The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed-Round.
Height: 40 cm–55 cm.
Width: 40 cm–50 cm.
Stem:
*Length.*—5 cm–8 cm.
*Diameter.*—0.6 cm–0.8 cm.
*Texture.*—Rough.
*Color.*—Near 137C.
Branching characteristics: Free branching and spreading.
Lateral branches:
*Length.*—8 cm–15 cm.
*Diameter.*—0.6 cm–0.7 cm.
*Texture.*—Slightly pubescent.
Number of breaks from pinch: 7–15.
Response time: Near 9 weeks natural season.
Vigor: Medium/Short.
Shelf life: Near 26 days.
Disease (susceptibility/resistance observed): None observed to date.
Pest (susceptibility/resistance observed): None observed to date.
Drought and temperature (susceptibility/resistance observed): None observed to date.
Growth retardant type and treatment: No treatment necessary.
The plants were grown for 9 weeks in natural season conditions.

Propagation:
*Type.*—Vegetative Propagation via Stem cuttings.
*Time to rooting.*—12 days with soil temperatures of 70° F.
*Rooting habit.*—Fine and Fibrous.

Foliage

Number of leaves per lateral branch: 7–15.
Compound or single: Single.
Arrangement of leaves: Alternate.
*Shape of leaf.*—Typically 5 lobed ovate.
*Size of leaf.*—Width: 2.5 cm–4.0 cm. Length: 4 cm–6.5 cm.
*Leaf apex.*—Acute.
*Base.*—Obtuse.
*Attachment.*—Petioled.
*Aspect.*—Slightly undulating.
*Margin.*—Palmately lobed.
*Surface characteristics.*—Top: Slightly Pubescent. Bottom: Slightly Pubescent.
Petiole:
*Color.*—Near 138A.
*Length.*—1.0 cm–2.0 cm.
*Diameter.*—0.3 cm–0.5 cm.
Venation: Net. Prominent mid vein at underside.
*Color.*—Upper side: near 138B. Under side: near 138B.
Color:
*Mature leaf, upper side.*—Near 137A; under side: near 137C.
*Young leaf, upper side.*—Near 137A; under side: near 137C.

Flower

Flower appearance: Matte.
Flower type: Single.
Flower form: Flat.
Flower shape: Round.
Flowering habit: Cyme.
Number of blossoms per branch: 7–12.
Typical and observed flowering season: Natural season between August and September.
Inflorescence form: Corymbiform.
*Depth of fully expanded blossoms.*—1 cm–1.5 cm.
*Diameter of fully expanded blossoms.*—2.5 cm–3.5 cm.
*Diameter of disc.*—0.5 cm–0.7 cm.

Phyllaries:
*Number.*—22–25.
*Color.*—Near 137B.
*Length.*—0.4 cm–0.7 cm.
*Width.*—0.1 cm–0.2 cm.
*Texture/appearance.*—Dull/Pubescent.

Peduncle: Peduncle length is shortest at the terminal flower and progressively longer down the stem; longest length is on average 13 cm, shortest length is on average 7 cm.
*Length.*—7 cm–13 cm.
*Diameter.*—0.4 cm–0.6 cm.
*Angle from stem.*—20°–25°.
*Color.*—Near 138A.
*Surface.*—Pubescent.
*Habit.*—Slightly curving.
*Strength.*—Medium.

Pedicel:
*Length.*—Terminal: 5 cm–7 cm; lateral: 11 cm–13 cm.
*Diameter.*—0.3 cm–0.6 cm.
*Color.*—Near 137A.
*Surface.*—Slightly pubescent.
*Habit.*—Slightly curving.
*Strength.*—Medium/Strong.

Ray florets:
*Form/shape.*—Straight.
*Texture/appearance.*—Shiny.
*Number per flower.*—35–40.
*Length.*—1.0 cm–1.4 cm; Width: 0.7 cm–0.9 cm.
*Apex.*—Round.
*Base.*—Tubular.
*Margin.*—Entire.

Disc florets:
*Form/shape.*—Cylindrical.
*Texture/appearance.*—Matte.
*Number per flower.*—110–130.
*Length.*—0.5 cm; Width: 0.1 cm.
*Diameter of disc.*—0.8 cm–1.3 cm.

Fragrance: Slight.

Flower bud (at onset of color):
*Length.*—1.0 cm.
*Diameter.*—0.6 cm–0.8 cm.
*Form/shape.*—Ball shaped/Slightly flattened.

General flower color:
1. *Ray florets, upper side.*—Immature: near 51C. Mature: near 56A. Older/Fading: near 56B.
2. *Ray florets, under side.*—Immature: near 51C. Mature: near 56A. Older/Fading: near 56B.
3. *Disc florets.*—Immature: near 15B. Mature: near 16A. Older/Fading: near 22A.
4. *Bud.*—Near 50B.

Flower progression with age; Flowers fade uniformly with age.

The lastingness of bloom is about 26 days.

Reproductive Organs

Gynoecium present on Ray and Disc florets.

Ray florets per individual flower:
*Pistil number.*—20–25 observed.
*Stigma color.*—Near 12A.
*Stigma shape.*—Forked.
*Style color.*—Near 144A.
*Style length.*—0.2 cm–0.3 cm.

Disc florets per individual flower:
*Pistil number.*—70–80 observed.
*Stigma color.*—Near 12B.
*Stigma shape.*—Forked.
*Style color.*—Near 144A.
*Style length.*—0.2 cm–0.3 cm.

Androecium present on Disc florets only per individual flower.

Disc florets per individual flower:
*Stamen number.*—30–40 observed.
*Anther shape.*—Globular.
*Anther color.*—Near 14B.
*Pollen color.*—Near 14A.
*Pollen quantity.*—Medium.

Fruit and seeds: None observed.

What is claimed is:

1. A new and distinct variety of *Chrysanthemum* plant, substantially as described and illustrated herein.

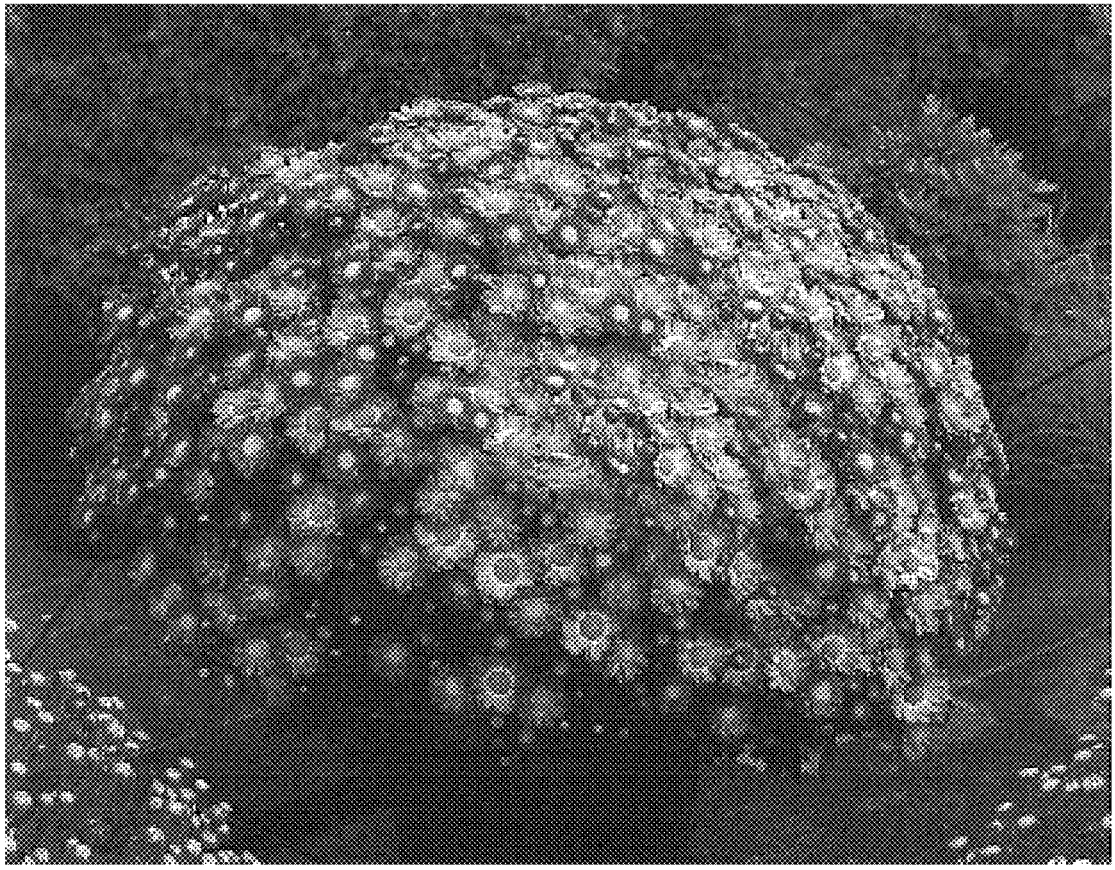

* * * * *